(12) United States Patent
Jansen et al.

(10) Patent No.: US 7,169,125 B2
(45) Date of Patent: Jan. 30, 2007

(54) METHOD AND A SYSTEM FOR ADMINISTERING MUSCLE RELAXANT TO A PATIENT (75) Inventors: Willem Jansen, LJ Arnhem (NL); Douglas John Eleveld, Groningen (NL); Søren Anders Larsen, Odense SV (DK)

(73) Assignee: Akzo Nobel, N.V., Arnhem (NL)

( * ) Notice: Subject to any disclaimer, the term of this patent is extended or adjusted under 35 U.S.C. 154(b) by 205 days.

(21) Appl. No.: 10/468,312

(22) PCT Filed: Feb. 19, 2002

(86) PCT No.: PCT/DK02/00111

§ 371 (c)(1),
(2), (4) Date: Aug. 14, 2003

(87) PCT Pub. No.: WO02/066103

PCT Pub. Date: Aug. 29, 2002

(65) Prior Publication Data

US 2004/0068229 A1 Apr. 8, 2004

(30) Foreign Application Priority Data

Feb. 19, 2001 (EP) .......................................... 01610012

(51) Int. Cl.
*A61M 31/00* (2006.01)

(52) U.S. Cl. ...................................................... 604/66
(58) Field of Classification Search ................. 604/65, 604/66, 67, 131, 132, 133, 134–135, 151, 604/154, 156, 511, 512; 128/DIG. 12, DIG. 13
See application file for complete search history.

(56) References Cited

U.S. PATENT DOCUMENTS

| 3,513,834 | A | * | 5/1970 | Suzuki et al. ................ 600/544 |
| 3,810,457 | A | * | 5/1974 | Boltcher et al. ............. 600/554 |
| 4,064,870 | A | * | 12/1977 | Dumitrescu et al. ........ 600/554 |
| 4,166,452 | A | * | 9/1979 | Generales, Jr. ............. 600/554 |
| 4,457,750 | A | | 7/1984 | Hill |
| 4,502,490 | A | * | 3/1985 | Evans et al. ................. 600/593 |
| 4,533,346 | A | | 8/1985 | Cosgrove, Jr. et al. |
| 4,570,640 | A | * | 2/1986 | Barsa .......................... 600/554 |
| 5,061,234 | A | | 10/1991 | Chaney |
| 5,368,042 | A | | 11/1994 | O'Neal et al. |
| 5,540,235 | A | | 7/1996 | Wilson |
| 5,843,134 | A | | 12/1998 | Thong et al. |
| 5,856,929 | A | | 1/1999 | McClendon et al. |
| 5,935,099 | A | | 8/1999 | Peterson et al. |
| 5,957,860 | A | * | 9/1999 | Rodiera Olive ............. 600/546 |
| 6,067,467 | A | | 5/2000 | John |

FOREIGN PATENT DOCUMENTS

| EP | 0 787 506 A1 | 8/1997 |
| EP | 1 059 064 | 12/2000 |

OTHER PUBLICATIONS

Mason D G et al: "Automated Delivery of Muscle Relaxants using Fuzzy Logic Control"; IEEE Engineering in Medicine and Biology Magazine, US, IEEE Inc. New York, vol. 13, No. 5, Nov. 1, 1994, pp. 678–686.

* cited by examiner

*Primary Examiner*—Manuel Mendez
(74) *Attorney, Agent, or Firm*—William P. Ramey III (57) ABSTRACT The invention relates to a system for administering muscle relaxant to a patient. The system includes an infusion pump adapted for delivering said muscle relaxant to a patient, and a controller adapted for controlling the operation of said infusion pump on the basis of at least one received input value. Further the system includes measuring means adapted for continuously measuring the effect of said muscle relaxant on the patient and adapted for supplying a value representing said measured effect as said input value to said controller. According to the invention, on basis of said at least one input value, said controller is adapted for selecting a control value from a set of predetermined control values as the value to be used for controlling said infusion pump. The invention also relates to a method of administering muscle relaxant to a patient and to a testing apparatus adapted to be used for testing the automatic operation of a system for administration of muscle relaxant to a patient.

14 Claims, 6 Drawing Sheets

| Index Values | 10 | 15 | 25 | 45 | | 45 | 15 | 10 |
|---|---|---|---|---|---|---|---|---|
| | $I1_0$ | $I1_1$ | $I1_2$ | $I1_3$ | | $I1_{n-2}$ | $I1_{n-1}$ | $I1_n$ |

FIG. 3A

| $I2_m$ | 10 | 15 | 5 | 10 | | 90 | 92 | 95 |
|---|---|---|---|---|---|---|---|---|
| $I2_{m-1}$ | 15 | 25 | 15 | 22 | | 56 | 87 | 85 |
| $I2_{m-2}$ | 45 | 55 | 65 | 33 | | 68 | 82 | 75 |
| | | | | | | | | |
| $I2_2$ | 25 | 35 | 35 | 53 | | 33 | 72 | 64 |
| $I2_1$ | 15 | 20 | 30 | 23 | | 40 | 45 | 35 |
| $I2_0$ | 10 | 15 | 25 | 45 | | 45 | 15 | 10 |
| Index Values | $I1_0$ | $I1_1$ | $I1_2$ | $I1_3$ | | $I1_{n-2}$ | $I1_{n-1}$ | $I1_n$ |

METHOD AND A SYSTEM FOR ADMINISTERING MUSCLE RELAXANT TO A PATIENT

RELATED APPLICATION

This application is a National Stage of International Application No. PCT/DK02/00111, filed Feb. 19, 2002.

TECHNICAL FIELD

The present invention relates to a system for administering muscle relaxant to a patient, said system including:
an infusion pump adapted for delivering said muscle relaxant to a patient,
a controller adapted for controlling the operation of said infusion pump on the basis of at least one received input value, and
measuring means adapted for continuously measuring the effect of said muscle relaxant on the patient, and adapted for supplying a value representing said measured effect as said input value to said controller.

The invention also relates to a method for administering muscle relaxant to a patient.

BACKGROUND ART

Skeletal muscle relaxants are administered to patients undergoing surgical procedures in order to facilitate intubation and to provide muscle relaxation in the surgical field.

When muscle relaxants are used in the operating room, according to current practice, the muscle relaxant is injected into the patient manually by an anesthesiologist. The effect of the muscle relaxant on the patient, i.e. the so-called relaxation, is assessed either by clinical observations alone; subjectively quantified by use of a peripheral nerve stimulator (PNS); or it can be measured objectively by means of a neuromuscular transmission monitor. When the clinical observations/judgements or data from the monitor device indicate that the patient is sufficiently relaxed, the patient may be intubated to facilitate automatic ventilatory support and the surgical procedure may begin.

When the effect of the muscle relaxant begins to disappear or decrease, meaning that the patient is becoming less relaxed, additional doses of muscle relaxant may be administered to the patient to ensure sufficient surgical relaxation and hereby enable the procedure to continue. The process of administering muscle relaxant to the patient is repeated during the entire surgical intervention. When the intervention is finished, monitoring of the patient must continue during the recovery phase. This is required, as the patient is not capable of breathing on his/her own, until the muscle relaxation effect has disappeared. During the surgical intervention and the recovery phase the patient is ventilated to support proper supply of oxygen. When the physician judges that the patient is sufficiently recovered and the muscular function has returned, extubation will take place and the patient will breathe on his/her own. It is noted that the physician may perform the above-mentioned judgements by means of clinical observations, by use of PNS, or by use of a neuromuscular transmission monitor.

As an alternative to the drug injection performed manually by an anesthesiologist, a semi-automatic infusion system can be used. Such a system is disclosed in U.S. Pat. No. 5,256,156 to Kern et al. This system, which is an infusion system for administration of neuromuscular agents and the like to a patient, includes a microcomputer-controlled infusion pump with a data input pad. A clinician enters the desired paralysis level and performs periodically an electro-stimulation test to determine the actual paralysis level of the patient. This information is entered into the system by the physician, which system then calculates and administers a new dosage.

On basis of an input value, the controller may be adapted for selecting a control value from asset of predetermined control values as the value to be used for controlling said infusion pump.

U.S. Pat. No. 5,843,134 describes a medication-dosing device having at least one sensor for detecting the physical state of a patient and for outputting a corresponding measured value, and an evaluating and controlling device adapted for determining a therapy control variable from the measured value. The device comprises an addressable dosage-data memory including an association table for heart rate-medication dose.

"Automated Delivery of Muscle Relaxants using Fuzzy Logic Control", Mason D. G. et al., IEEE Engineering in Medicine and Biology Magazine, US, IEEE Inc. New York, vol. 13, no. 5, 1 Nov. 1994, Pages 678–686, describes a fuzzy logic controller adapted for controlling the delivery of muscle relaxant to a patient. The fizzy logic controller includes a performance index look-up table. The inputs usually considered are the error from a desired reference value, i.e. the difference between a measured level of the desired level of relaxation and the measured level of relaxation, and the change in this error. The output is either considered to be the controller output or the change in controller output. The level of relaxation of the patient is measured by supplying a stimulation pulse to the patient and measuring the level of the resulting muscle reaction pulse.

Such systems can be useful, but some have the drawback of requiring constantly monitoring of the neuromuscular function and manually entering the actual measured paralysis level of the patient, which is quite demanding for the personnel in the operation room. Other systems have the drawback of relying on one resulting reaction pulse only and require rather complex implementation means which can be cumbersome to verify completely in all situations. Consequently the patient may be given more muscle relaxant than actually required for the surgical procedure. Alternatively if the patient is given too little muscle relaxant, the surgical conditions will also be sub-optimal. None of these situations are desirable, neither with respect to the comfort of the patient or from a surgical point of view. In addition these situations are undesirable from an economic point of view. The desire to use a complete automated neuromuscular blocking agent delivery system was also mentioned in the above U.S. Pat. No. 5,256,156 to Kern et al. However according to Kern et al., such a system is too cumbersome and expensive to be clinically useful.

BRIEF DESCRIPTIONS OF THE INVENTION

It is an object of the invention to provide an improved system for administering muscle relaxant to a patient compared to the systems known from the prior art.

According to the invention, a system of the above-mentioned art is described, wherein said measuring means is adapted for stimulating a muscle of the patient by a number of succeeding electric or magnetic pulses, for measuring the resulting muscle reaction pulses and for using the number of muscle reaction pulses as said input value.

The invention, which overcomes the prejudice of the prior art that the construction of a system for administering muscle relaxant to a patient or an automated neuromuscular blocking agent delivery system is too cumbersome and expensive to be clinically useful, is based on the fact that infusion can be controlled by use of a predetermined set of control values. Hereby a system according to the invention is made reliable as the operation of the infusion pump is restricted to the operation associated with the predefined control values, i.e. a stable and reliable system is obtained. In addition, as the operation of the infusion pump is restricted to the operation associated with the predefined control values, the relatively simple system resulting therefrom can easily be tested in order to prove a desirable operation. This is of major interest in relation to clinical use as the desirable operation of the system can be validated and documented.

A system according to the invention has been found to have the following advantages compared to prior art systems for administering muscle relaxant to a patient. In addition to the optimal surgical conditions which can be achieved, a better control of the effect of the drug is obtained compared to the use of manual dosing or the use of known semi-automated systems. In addition less workload is imposed on the staff, and, as the dosing of the drug does not require constant attention of an anesthesiologist, an environment wherein more attention can be given to the well-being of the patient is achieved. Furthermore, an optimal drug load to the patient can be achieved, i.e. a minimal amount of drug to obtain the effect desired can be used, and as a result the fastest possible patient recovery after stop of drug infusion can also be obtained.

Furthermore, as the system according to the invention is adapted for stimulating a muscle of the patient by a number of succeeding electric or magnetic pulses, for measuring the resulting muscle reaction pulses and for using the number of muscle reaction pulses as said input value, the patient's level of relaxation can be measured in a both simple, reliable and fail-safe manner. The invention is based on the fact that the resulting number of muscle reaction pulses has been found to be a good indication of the patient's muscle relaxation. Furthermore, this solution enables a simple interface with the controller as the resulting number of reaction pulses may be used as input; i.e. the operation of the infusion pump may be controlled using the resulting number of reaction pulses.

According to a preferred embodiment of the invention, the system includes a memory with an array of one or more dimensions holding said set of predefined control values, where said controller is adapted for selecting a control value from said set of control values by indexing said array by said at least one input value and/or at least one value derived therefrom. Hereby, as the contents of an array can be indexed in a simple way, the control values can easily and rapidly be retrieved and used for the control of the infusion pump.

Preferably, said array is adapted for including one or more mathematical functions as a representation of a number of said control values. Hereby, as a number of control values may be stored as a reduced number of mathematical functions compared to the number of control values represented hereby, the memory requirement is kept at a minimum. Further, when continuously mathematical functions are used, a control value between two discrete indexing values may easily be computed without interpolating using two or more discrete control values.

According to another preferred embodiment of the invention, said controller is adapted to select the control value or a representation thereof on the basis of at least one index value derived from two or more previously received input values. Preferably said at least one index value is derived as the mean value of two or more previously received input values. Hereby a high resolution of the received input value is obtained in a simple manner even when only a single input value is received from the measuring means. For example, even when a simple input value of integer type is received from the measuring means, a higher resolution is obtained by use of the value derived from a number of previously received values.

According to a preferred embodiment of the invention said measuring means is adapted for comparing two or more of said measured muscle reaction pulses with two or more corresponding reference muscle reaction pulses or a representation thereof, and determining the difference between as an effect of direct muscle stimulation. Hereby, a possible direct stimulation of the muscle, e.g. due to an incorrect locations of the stimulation means in relation to the patient, can be detected by the system.

Preferably, said system is adapted for subtracting said effect of direct muscle stimulation from the measured effect of said muscle relaxant delivered to the patient. Hereby, it is ensured that a correct determination of the effect of the muscle relaxant on the patient is performed, and as a consequence, that an optimal amount of muscle relaxant is delivered to the patient.

According to yet another preferred embodiment, said infusion pump is adapted for incepting a container including muscle relaxant, and for delivering muscle relaxant from said container to a patient, and by further including identification means adapted for identifying, the container incepted in the infusion pump. Hereby it can easily be ensured that the desired container, i.e. a container including the desired type of muscle relaxant, is incepted in the infusion pump and an undesired use can be avoided.

When said controller furthermore includes a plurality of sets of control values, and said controller is adapted for selecting a set of control values to be used on the basis of the identification of the container incepted in the infusion pump, the operation of the system can be optimized in accordance with the given container and hereby with the contents of the given container.

Preferably, said controller includes a plurality of sets of control values, and said controller is adapted for selecting a set of control values to be used on the basis of a received value representing the type of intervention performed or to be performed or is dependent upon certain specific patient characteristics. This solution is of interest as a further security check can be performed based on the received information. The security may be further improved, when drug identification information and/or patient specific information is also received in the system or accessible by the system.

As described above the invention also relates to a method of administering muscle relaxant to a patient, said method including:

delivering said muscle relaxant to a patient, where said delivering is controlled on the basis of at least one received input value, and continuously measuring the effect of said muscle relaxant on the patient, and supplying a value representing said measured effect as said input value for said controlling, wherein:

said controlling is performed using a set of predetermined control values, and further including selection of a control value from said set of control values as the value to be used for controlling said infusion pump, where said selection is based on said input value and/or a value derived therefrom.

The advantages of the method according to the method described above and according to the methods of the preferred embodiments of claims 12 and 13 will not be described as they are already described in connection with the corresponding system claims.

Furthermore, the invention relates to a testing apparatus adapted to be used for testing the operation of a system for administering muscle relaxant to a patient. This is of major interest as the test of such systems has to be performed and documented prior to the actual use. Therefore, a system which can ease this cumbersome task is of major interest.

The testing apparatus according to the invention is characterised by including:

an input emulator adapted for receiving muscle relaxant from said system;

a testing signal receiver adapted for receiving a testing signal from said system;

a test controller adapted for continuously determining a value representing the present level of relaxation of a patient simulated by the apparatus, said value being determined on basis of the amount of relaxant infused and the time elapsed since infusion; and a response emulator adapted for generating an output signal in response to said received testing signal, said output signal reflecting the present state of relaxation.

A testing apparatus according to the invention enables an evaluation and validation of the widest possible range of patient interactions in a pre-clinical in-vitro setting. Further advantages as well as preferred embodiment of the system according to the invention will be described in the detailed description below.

BRIEF DESCRIPTION OF THE DRAWING

Other features and advantages of the present invention will become apparent from the following description of the preferred embodiments, taken in conjunction with the accompanying figures wherein.

BEST MODE FOR CARRYING OUT THE INVENTION

Figure 1A:
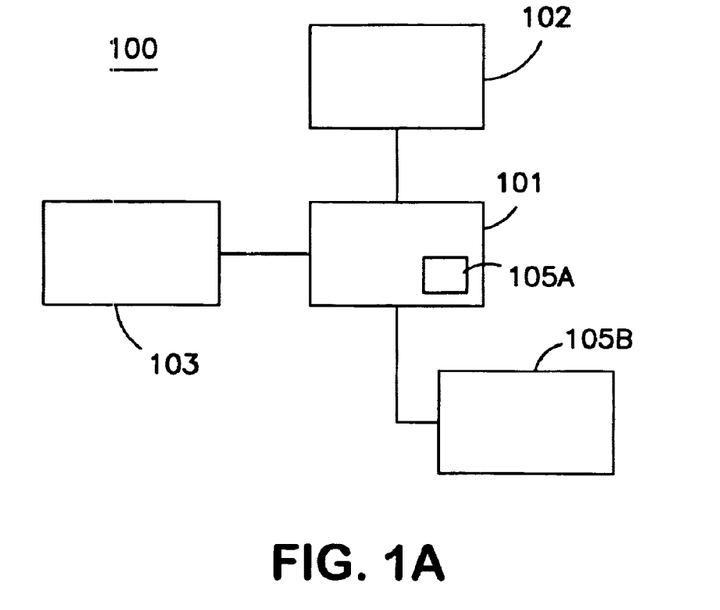
FIG. 1A is a system according to the invention.

FIG. 1A is a system according to the invention, i.e. a system for administering muscle relaxant to a patient. The system 100 includes an infusion pump 102, a controller 101, and measuring means 103. The infusion pump 102 is adapted for delivering the muscle relaxant to a patient, and the measuring means 103 is adapted for continuously measuring the effect of the muscle relaxant on the patient. The measuring means 103 is connected to the controller 101, e.g. via a data channel connection, and is adapted for supplying a value representing the measured effect of the muscle relaxant on the patient to the controller 101. For example, the data channel connection can be implemented as an RS-232 connection. The controller 101 is adapted for controlling the operation of said infusion pump 102 on the basis of the value received from the measuring means 103.

The controller 101 includes a first memory 105A holding a set of predetermined control values, and the controller is adapted for selecting a control value from the set of control values as the value to be used for controlling said infusion pump 102. The selection of the control values from the set of control values is described in the following. In another preferred embodiment the system includes a second memory 105B in which the predetermined control values or at least a part thereof is located. As illustrated in the figure, the controller is connected to the second memory or is adapted to being connected thereto when needed. For example, the second memory 105B may be a hard disc drive, a RAM, a ROM, a CD-ROM, or another type of memory being able to hold predetermined control values.

In a preferred embodiment, the controller and the second memory 105B is connected via a network connection. This enables a number of systems to share the same second memory, and hereby the predetermined control values can be stored and updated centrally. Further, this is advantageous as the size of a local memory, e.g. located in the controller or in direct connection with the controller, can be reduced to a size enabling it to hold a single set of control values, for example. The external memory on the other hand can hold a large number of sets of control values, and the system can be adapted to retrieve the set of control values to be used either on the ran or prior to the administration of the muscle relaxant to the patient. Due to safety the latter of these two solutions is often advantageous.

Figure 1B:
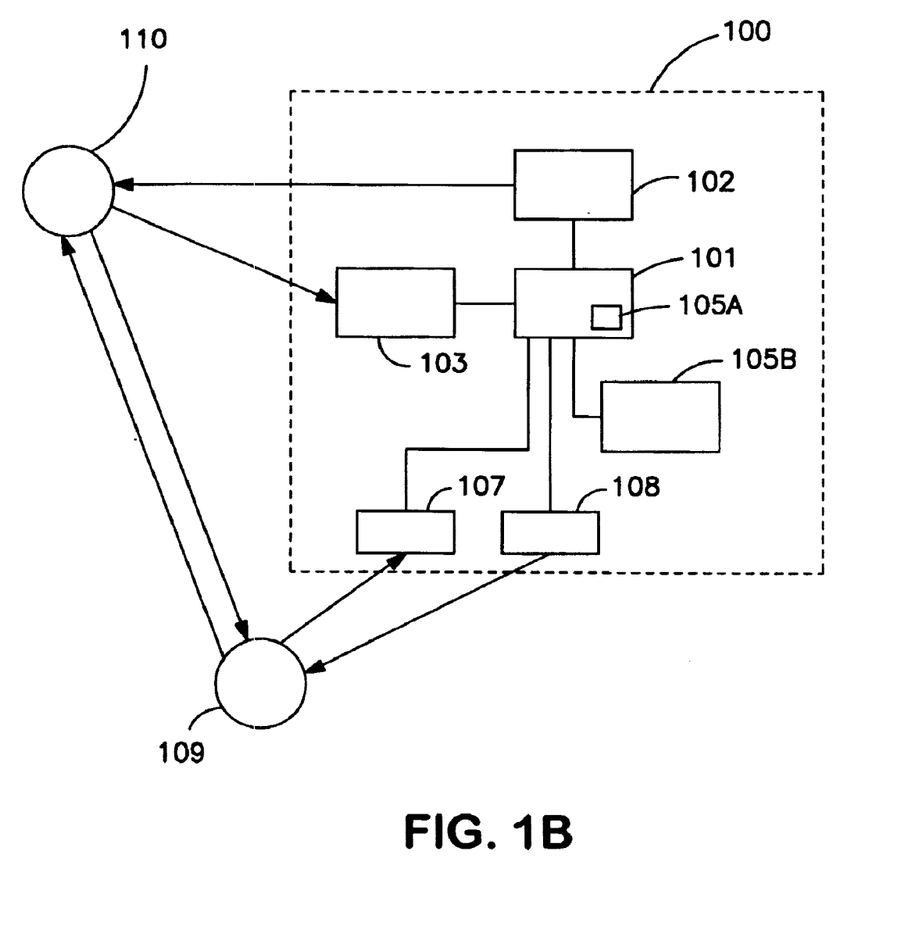
FIG. 1B illustrates a closed loop system according to the invention.

As illustrated in FIG. 1B, the system according to the invention is a closed loop system wherein the controller 101 is connected to the infusion pump 102. When the infusion pump 102 is connected to a patient muscle relaxant can be delivered to the patient via the infusion pump 102 under the control of the controller 101. The measuring means 103 is continuously measuring the effect of said muscle relaxant on the patient. The measuring means 103 is also connected to the controller 101 to which it supplies the obtained measurements. The controller 101 uses the received measurements to control the amount of muscle relaxant to be delivered to the patient.

The controller 101, which is also called a controller unit in the following, is adapted for controlling the operation of said infusion pump 102 on the basis of a received input value. In the example shown, the controller unit 101 receives information about the patient's state of relaxation from the measuring means 103 and inputs the received information to a control array containing values for a predefined desired level or target level. Based upon the actual level of relaxation and the specific selected control values, the controller 101 determines the amount of relaxant to be used in the further dosing in order to reach the target state. The controller unit 101 then commands the pump 102 to maintain, increase or decrease the amount of relaxant infused to the patient. The determination is performed by use of a control algorithm which is described in the following.

The measuring means 103, which is also denoted the neuromuscular transmission monitor 103 or simply the monitor 103 in the following, measures the patient's level of relaxation, and supplies the measured effect as one or more input values to the controller 101. In a preferred embodiment of the invention, the measurement is performed by applying a small electrical stimulation pulse to the patient and measuring the muscle reaction as the result of the applied stimulation. It is noted that the stimulation may also be applied to the patient in other ways, e.g. by a magnetic excitation of the nerve controlling the muscle to be elicited.

The measuring means 103 includes means for applying a small electrical impulse (stimulation) to the patient and measuring means, such as an acceleration transducer, which is adapted for measuring the muscle reaction as the result of electrical stimulation. The adductor pollicis muscle is normally used for routine neuromuscular transmission monitoring, and in this case the muscle reaction generates a movement of the thumb and an acceleration transducer measures the acceleration of the thumb. It is noted, that other muscles can be used as well in order to measure the relaxation of the patient; e.g. the orbicularis occuli, the corrugator supercilii or the flexor hallucis brevis etcetera muscles may be used.

The size of the muscle reaction is proportional to the patient's state of relaxation. Muscle reaction can be quantified either by measuring the force (MMG) from the muscle reaction (isometric), the generated acceleration (AMG), the evoked muscle potential (EMG) or measuring the evoked acoustic muscle signal from the contraction (Phono myography). The monitor. 103 transmits the measured relaxation data to the controller 101 of the system.

The neuromuscular transmission monitor 103 may be derived from an already commercial available device (e.g. TOF-Watch® SX from NV Organon), with adaptations to accommodate for the actual application. This microprocessor-controlled monitor is designed with the necessary redundant protection against stimulation (current) that is too high, open circuit stimulation, watchdog circuitry for microprocessor monitoring etc. The monitor 103 transmits the measured relaxation data to the controller unit 101 of the system.

The infusion pump 102 may be a syringe pump, i.e. a pump including a mechanism for driving or pushing a normal syringe, or a volumetric pump. A volumetric pump can be constructed either as a roller mechanism—also called a peristaltic pump—or a set mechanical fingers actuating a flexible tubing containing the drug or a membrane pump.

The pump 102 to be used may be derived from a standard commercially available pump, with adaptations to identify the drug being infused by the system. Like the other elements in the system, the pump 102 may be microprocessor controlled and designed with the required redundancy towards occlusion, drug container in place, near empty detection, drug container identity etc. The controller unit 101 of the system will command/control the infusion of drug via the pump 102.

The controller unit 101 receives information about the patient's state of relaxation from the monitor 103 and inputs the received values to a control array containing values for the desired level of relaxation. Based upon the actual level of relaxation and the desired level from the specific selected control array, i.e. the target level, the controller 101 determines—by use of the control algorithm—further dosing to reach the target state of relaxation. The controller unit 101 then commands the pump 102 to maintain, increase or decrease the amount of relaxant infused to the patient.

The controller unit of the system may also contain various safety mechanisms to ensure that possible errors will not result in a substantial over/under dosing of the patient. As for the other elements in the system, redundancy mechanisms can also be incorporated in the controller.

Finally, the controller unit 101 also contains the control interface towards the user and performs registration of all events and data being registered during use. This is indicated in FIG. 1B wherein the system also includes a user interface which may be used by a user 109, such as a physician being in contact with the patient 110. As illustrated, the user interface may include input means, such as a keyboard 107, by which the user 109 may be able to input relevant information and output means, such as a display, by which the user 109 can be presented by system information, e.g. information of the patient's relaxation. For example, for security reasons, the user 109 may be able to adjust or even halt the regulation.

The measuring means is adapted for stimulating a muscle by a single or a number of succeeding electric or magnetic pulses, for measuring the resulting muscle reaction pulses, and for using the value of the reaction pulses and/or the number of muscle reaction pulses as the input value to the controller. In one embodiment the stimulation includes a number of pulses which are repeated at a constant rate, but in another embodiment the stimulation includes a number of pulses which are repeated at a varying rate.

As described above, the controller or controller unit 101 is adapted for controlling the operation of said infusion pump 102 on the basis of at least one received input value. The input value or the input values are received from the measuring means 103 and are used in order to retrieve the control values to be used when controlling the operation of the system. The control values are retrieved from the first or second memory 105A, 105B.

According to another preferred embodiment of the invention, the controller 101 is adapted to select the control value on the basis of an index value derived from the last and/or two or more previously received input values, and preferably from a set of index values derived from a combination of the last and two or more previously received input values. Preferably said index value is derived from the mean value of two or more previously received input values. Hereby a high resolution of the received input value is obtained in a simple manner even when only a single input value is received from the measuring means. For example, even when a simple input value of integer type is received from the measuring means, a higher resolution is obtained by use of the last value and a combination of values derived from a number of previously received values. It is noted that the index value can be derived from previously received input values in other ways as well, e.g. as exponential average, gradient (slope), higher order derivatives.

Figure 2:
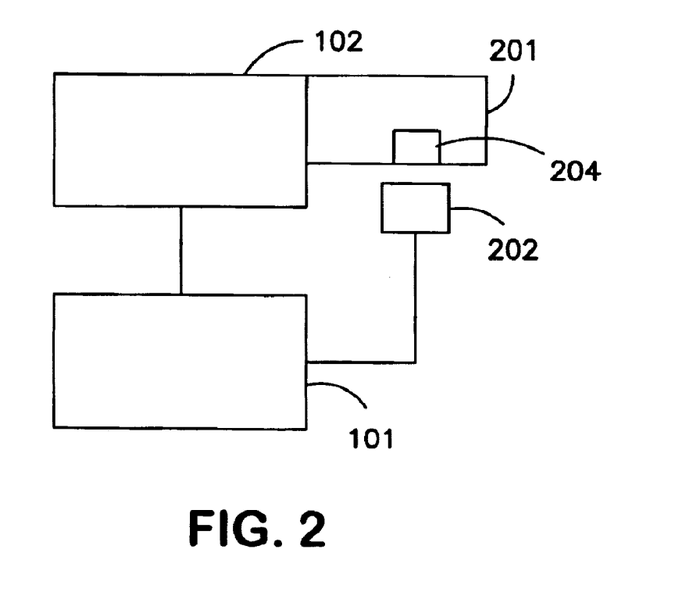
FIG. 2 illustrates the infusion pump part of a system according to the invention in more details.

FIG. 2 illustrates the infusion pump part of a system according to the invention in more details. As described previously, an infusion pump 102 being adapted to transfer muscle relaxant to a patient is connected to and controlled by a controller 101, such as a micro-processor. As illustrated in the figure, a drug container 201 containing a drug to be supplied to a patient may be attached to the infusion pump 102 which has been developed for this purpose. Hereby, the drug to be used can easily and quickly be replaced when needed. Even though only a single drug container is shown in the figure, a larger number of containers may be connected to a system according the invention if desired.

The infusion pump also includes supplying means connecting the infusion pump to the patient, e.g. via an infusion set supplying infusion fluids and the like to a vein of the patient. As illustrated in the figure, an identification of the drug container 201 incepted in the infusion pump 102 is performed by use of identification means 202 in the system. The identification means 202 is adapted for identifying the drug container incepted in the infusion pump 102 and hereby identifying the contents of the drug container 202. In a preferred embodiment, the identification is performed using a drug ID tag 204 attached to the drug container 201. The drug ID 204 tag contains information relating to the muscle relaxant in the drug container 201. For example, the drug ID tag 204 may include information, such as the type of drug, the date of production, the time of production, the date for last use, the time for last use, and/or concentration information.

The identification may be performed in a number of ways in which the drug container 201 holds identification information which can be read or received by identification means 202 located in the system. The ID tag 204 may include a bar code holding the identification information and consequently the system may include a bar code reader as an identification means 202. The identification may also be performed by use of other types of ID tags 204 and other types of identification means 202. The information means 202 may also be adapted to read or received identification information from other types of ID tags 204, such as reading of a magnetic stripe—contact reading, electronic reading of memory—electric contact reading, magnetic label—space readable (no contact required to label), RFID (Radio Frequency Identification)—chip with coil (magnetic actuation) or antenna (electrostatic actuation), and/or mechanic coding and mechanic reading. As will become clear from the following description, the possibility of identifying the drug container 201 is of major interest according to the invention. For example, based on a performed drug identification, an array of control values may be selected from a plurality of arrays of control values. The selection of an array of control values may also be based on a drug identification in combination with patient related information.

Figure 3A:
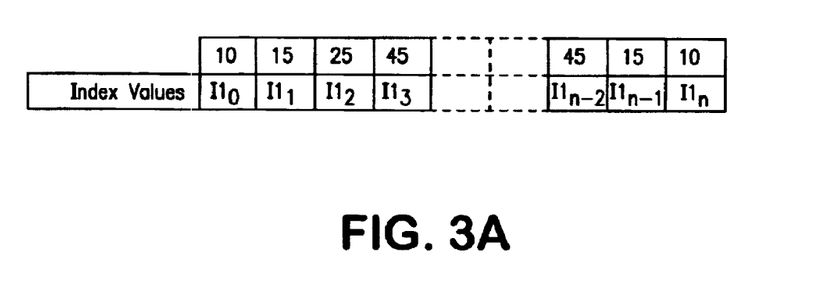
FIG. 3A is an example of a one-dimensional array holding a set of predefined control values.

FIG. 3A is an example of an array or table of one dimension holding a set of predefined control values. The system has access to the control values in the array and uses the control values in order to perform the drug delivery control. Therefore, the array may be located in the memory of the controller, and/or in another accessible memory. The control values of the array may be retrieved by use of an index value; e.g. using an input value reflecting the patient's state or relaxation or a value derived therefrom as an index value.

Figure 3B:
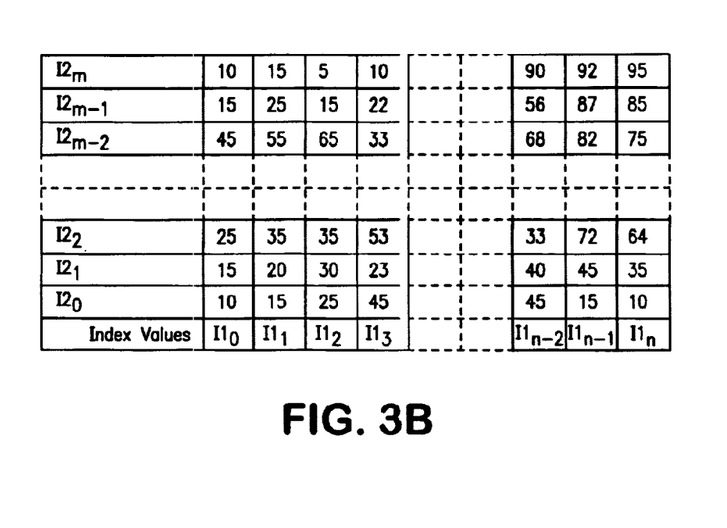
FIG. 3B is an example of two-dimensional array holding a set of predefined control values.

FIG. 3B is an example of two-dimensional array holding a set of predefined control values. In order to perform a look-up in the array or table, two index values may be used. A first index value may for example be used as a first entry, e.g. pointing out a row in the table, and a second index value may for example be used as a second entry pointing out a column in the table. As described in more details in the following, different values may be used as index values, e.g. a value reflecting the patient's state of relaxation or a value derived therefrom.

Figure 3C:
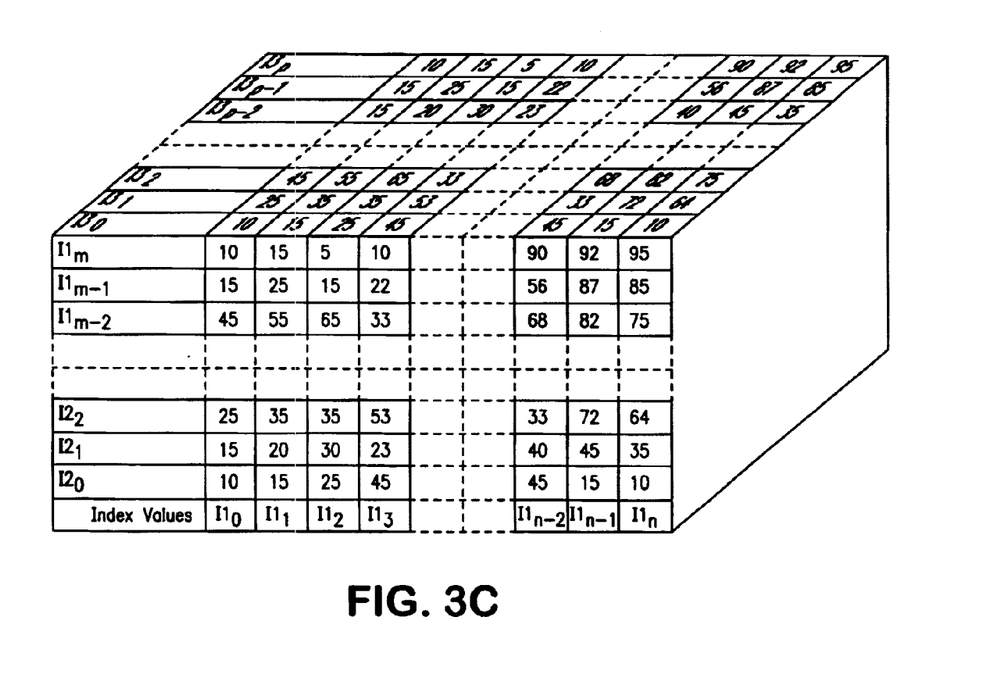
FIG. 3C illustrates a three-dimensional array holding a set of predefined control values.

FIG. 3C illustrates a three-dimensional array holding a set of predefined control values. According to the figure, the array may also be three-dimensional allowing three index values to be used when selecting a control value to be used. Likewise, an array of higher dimension may be used as well. The use of more dimensions enables the use of different parameters when selecting control values which may be advantageous, but in the preferred embodiment a dimension of two or three has been found optimal in most cases due to simplicity.

The relationship between one or more input values reflecting the state of relaxation of the patient in a given period of time or one or more values derived therefrom, and the control value to be supplied to the infusion pump in order to achieve or maintain a desired level of relaxation is very complex. The relationship can be described by a complex mathematical formula specifying a surface of control values in an n-dimensional space defined by the input values used and the values derived therefrom. As the mathematical relation is very complex, an array is used in order to define the control values.

Due to the complexity of the regulation system, the determination of the control values is very computation power demanding. Therefore, the array to be used when administrating muscle relaxant to a patient is predetermined, i.e. the computation of the control values is performed prior to the use of the system. For example, the manufacturer of the system may perform the computation as the computation time in this phase is less critical than the computation time during use of the system. By performing the computation or at least a major part thereof prior to the use of the system, the regulation may be performed sufficiently rapid to obtain a good regulation. Further, by predetermining the control values, a stable and secure system can be achieved as the behaviour in all possible situations can be tested.

In order to determine the control values to be used in an array, a large number of data sets describing a pharmacokinetic, pharmacodynamic patient model, i.e. a PK/PD-model, for a number of different persons are used. The PK/PD-model, which is known from the prior art, describes a given body's influences on a given drug supplied thereto (the pharmacokinetic part of the model), and how a given body reacts to a given drug concentration (the pharmacodynamic part of the model). For example, the pharmacokinetic part describes how quickly the supplied amount of drug is distributed (circulated) and eliminated in the body, whereas the pharmacodynamic part describes the effect (relaxation over time) related to a given drug concentration at the site of action for a given patient.

Based on a given target relaxation value the control values are calculated and selected in accordance to a number of requirement. The requirement must be selected in accordance with a number of decisions to be taken. The decisions may for example be related to the following topics: (1) the regulation time (fast/slow regulation), (2) the amount of overshoot acceptable prior to achieving the desired level of relaxation, (3) good performance on abnormal patients too, (4) immunity towards artifacts (noise) in the measurements. Depending on the choices made, the computation results in an array to be used when controlling the system. Further, the control values are selected in such a way that a stable control system is obtained, e.g. when a given level of relaxation is reached, the control values to be used shall ensure that no deeper or lower levels of relaxation can be achieved.

It is noted that an array of control values includes a number of discrete control values in the preferred embodiment, but other representations may be used as well, if desired. For example, an array including predefined mathematical functions being sufficient simple to practical use may be used as well.

Figure 4:
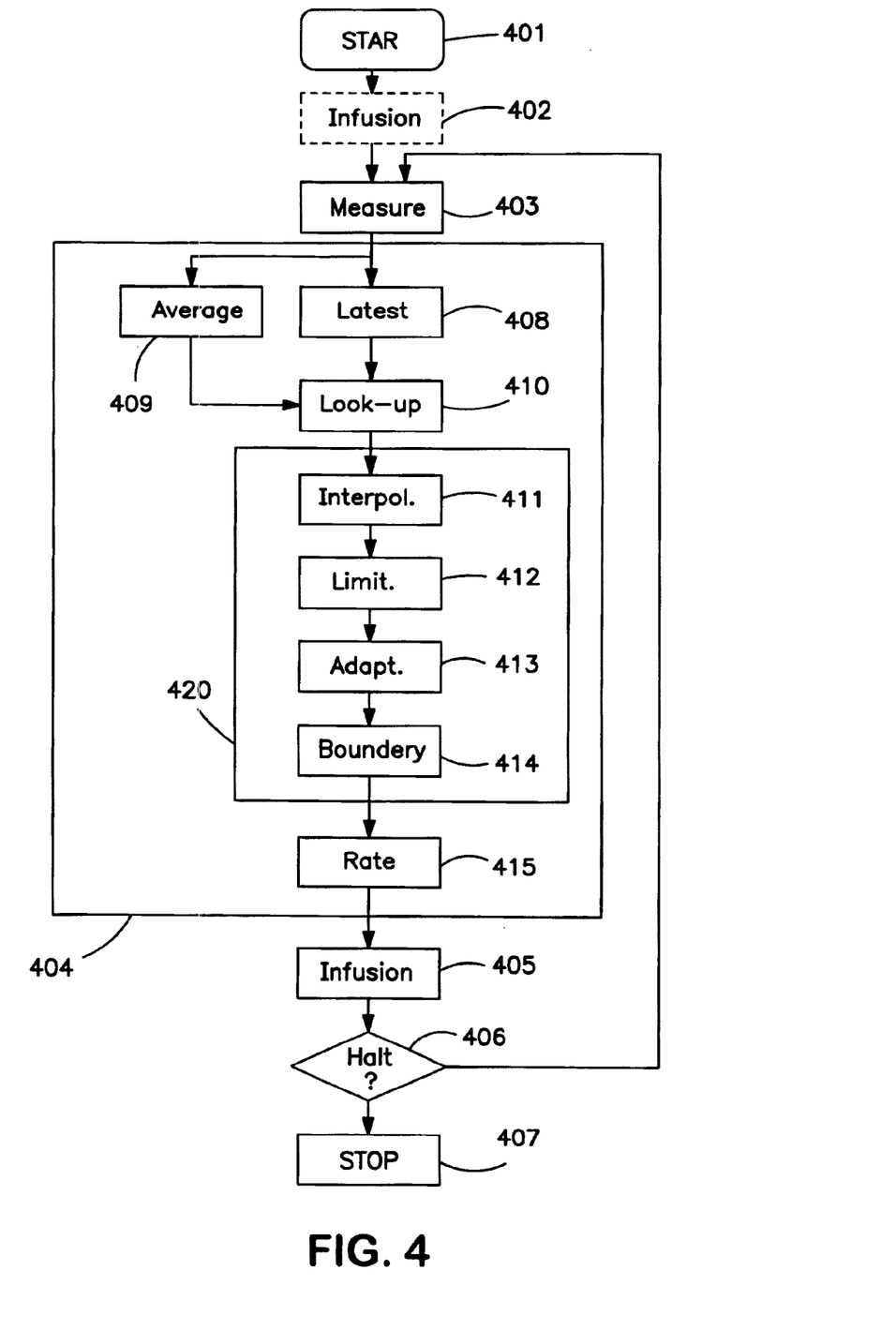
FIG. 4 illustrates a preferred control of the delivery of muscle relaxant to a patient.

FIG. 4 illustrates a method or control algorithm according to the invention, i.e. a method of administering muscle relaxant to a patient. The amount of muscle relaxant delivered to the patient is controlled continuously and the muscle relaxant is delivered to the patient by use of an infusion pump according to normal praxis. But it is noted that the drug may be delivered in other ways as well, e.g. by inhalation, transdermal delivery or alike, if the drug used enables such a solution. The measured effect of the supplied muscle relaxant on the patient is measured continuously, and a value representing the measured effect is supplied as an input value, which is used for controlling the delivering. The controlling is performed using a set of predetermined control values, and a control value from the set of control values is selected as the value(s) to be used for controlling said infusion pump. As will become clear from the following, the selection is based on said input value and/or a value derived therefrom.

After starting the control of the administering of muscle relaxant to a patient in step 401, the state of relaxation is measured in step 403. The measurement in step 403 may be performed in a number of ways according to the prior art, e.g. by a small electrical stimulation to the patient and measuring the muscle reaction as the result of electrical stimulation. Prior to the measurement performed in step 403, an initial predefined infusion of muscle relaxant to the patient may be performed in step 402, but it is noted that due to safety no initial infusion is normally performed prior to the determination of the relaxation in step 403. In step 404 the infusion rate to be used is determined, and in step 405 the infusion is started. It is noted that a continuous infusion enables a slowly changing drug delivery.

In another preferred embodiment a discontinuous drug delivery is performed in step 405, i.e. a given amount is infused in a given period of time, only. This latter solution enables a more quickly change in relaxation which is advantageous in some situations. In step 406 it is determined whether the regulation should be stopped, e.g. as a result of an input from a user demanding the regulation to be terminated. When this is not the case, the control is continued in step 403 in which the state of relaxation is determined as described above. It is noted that a delay is advantageously inserted between step 406 and step 403 hereby enabling the drug inserted to have an effect on the patient before determining the effect thereof. In the case in which the regulation process is halted the regulation is stopped in step 407. Step 406 illustrates that the regulation may be halted as a result of a polling performed. Advantageously, a halt command, e.g. as a result of a user pressing a stop button, may be initiated as an interrupt command.

As illustrated in the figure, the determination of the infusion rate in step 404 may be performed in the following way. The state of relaxation information or result obtained in step 403 is received as an input value in step 408 which is used as a first index value in step. 410. The state of relaxation information or result obtained in step 403 is also received as an input value in step 409. In step 409 an index value is derived from the last and a number of previously received input values, and the derived index value is used as a second index value in step 410. In the preferred embodiment the index is derived as the mean value of two or more previously received input values, e.g. as an average over a given interval of time such as two minutes. It is noted that the index value can be derived from previously received input values in other ways as well, e.g. as exponential average, gradient (slope), higher order derivatives based on a number of previously received input values.

In step 410 one or more control values are retrieved from a look-up table or array of control values using the index values from step 408 and 409. Based on the retrieved control value(s), the infusion rate is determined in step 415, and the infusion regulated in step 405. Likewise, the amount of muscle relaxant may be determined in step 415 and the determined amount may be infused in step 405, if the muscle relaxant is delivered discontinuously.

As can be seen from the figure, the control table look-up is performed from a table or array using two index values; i.e. a two-dimensional table as illustrated in FIG. 3B may be used. Such an implementation is advantageous as the control algorithm and becomes both very simple and highly predictive under all conditions. This is essential in relation to the verification and validation of the systems control performance.

Preferably, a number of index values is used when indexing the look-up table and the index values used are a number of received input values, e.g. the last and/or one or more previously received input values, and/or a number of index values derived from a number of received input values. The use of both one or more input values (preferably including the input value received lastly), and one or more values derived from one or more input values is advantageous and it enables the use of information reflecting the detected relaxation at a given point in time as well as information reflecting the development in relaxation over time. Hereby a smooth regulation towards a desired state of relaxation may be achieved in a simple manner. For example, the use of a two-dimensional array holding control values which is indexed by a first index value reflecting the present state of relaxation and a second index value determined as a mean value of a number of previous received values reflecting the state of relaxation over a given period of time has been found advantageous due to the simplicity, i.e. the low computation requirements during control.

The use of stimulation pulses when determining the patient's state of relaxation has been found very useful. In a preferred embodiment the patient is given a predefined number of stimulation pulses, e.g. a number of pulses between 1 and 10 or more, and the number of reaction pulses from the patient as a result of the stimulation is measured. Therefore, as the number of measured reaction pulses has been found to reflect the state of relaxation of the patient, the measured number is used as the input value in this embodiment, i.e. the selection of control values is based on the measured numbers of reaction pulses. This solution has been found advantageous both due to the simplicity and the robustness. When indexing an array of control values by use of an integer, i.e. the measured number of reaction pulses, the resolution of the regulation is limited, i.e. a maximum number of control values given by the number of stimulation pulses can be selected by use of a single input value. Therefore, according to the invention, the use of two or more input values has been found advantageous when indexing the array of control values. In fact, the use of one or more index values derived from one ore more input values has been found very useful as this solution enables a higher resolution. For example, the use of a mean value has been found very useful. As mentioned above, one or more input values may advantageously be used in combination with one or more values derived from a number of input values.

According to a preferred embodiment of the invention the control method also includes a processing and checking step (step 420). Step 420 includes the steps 411–414. In step 411 an interpolation, such as an linear interpolation, is performed using a number of control values received from the array. This is advantageous when a value to be used as an index value does not correspond to a possible input value. For example, if an array of control values is to be indexed by use of an integer value, e.g. in the interval between 1 and 5, and if the value to be used as an index value is a real value, e.g. the value 2.4, the control value to be used may be found by use of interpolation. For example, the control value corresponding to the control value associated with the control values 2 and 3 is retrieved from the array, and the control value corresponding to an index value 2.4 is found by interpolation, e.g. linear interpolation. In other words, the control values in the array can be regarded as points on a surface of control values in an n-dimensional space, where n is the dimension of the array of control values used. Therefore, the interpolation in step 411, can be regarded as an estimate of a point on the surface which is based on a number of known control points on the surface.

In the shown embodiment, step 411 is followed by step 412 wherein a volume/time limit check is performed. In step 412 it is ensured that the given patient is not given too much muscle relaxant; e.g. it is ensured that the amount of drug delivered to the patient during a predefined period of time do not exceed a given limit. Preferably, the limit is determined by the system by use of patient information such as body weight or other relevant information. For example, the limit is determined during initialisation of the system.

In step 413, a weight and concentration adaptation is performed on the control values to be used, i.e. the control value is adjusted according to the given situation, e.g. by use of patient and drug information. In the preferred embodiment, the control value and therefore the amount of drug supplied to the patient is adjusted according to the weight of the patient. Hereby, a heavy patient may be given a larger amount of drug, i.e. a larger control value is used, compared to a less heavy patient. Advantageously, the control value is adjusted according to the concentration of the drug used. Hereby, the same array of control values may be used in the two situations wherein a given drug used has a first and a second concentration, respectively. Therefore, the control values retrieved in the two situations can be adjusted differently when the first concentration is different from the second. This is of major interest as the memory requirement is reduced as a consequence of the possibility of using the same arrays of control values in different situations. The adaptation may also be based on other patient and/or drug related information if desired. The adjustment of the control values may be performed in different ways, e.g. as a linear adjustment. It is noted that other adjustment methods may be used in order to obtain the desired relaxation of the given patient when using the given drug. Advantageously, the adaptation in step 413 is performed using drug identification information received from the drug container, i.e. drug information such as type, concentration may be received from the drug container.

Finally, in step 414, a boundary check is performed. This check is performed as an additional security check ensuring that the amount of drug supplied to a patient does not exceed a specified limit at any time and in any situation. As mentioned in relation to the previous step, the drug identification information may also be used in this step. Hereby, the limit to be used can be based on information from the drug container. According to the preferred embodiment, in order to increase the safety of the system, the value used, e.g. a value derived or retrieved from the drug container information, is compared with values pre-stored in the system. If an unacceptable difference between the value to be used and the pre-stored value an alarm is activated, and if the delivery of the drug is in progress the delivery may be interrupted.

As mentioned in more details below, the drug identification information is advantageously retrieved in an initialisation phase, i.e. when initialising the system prior to the initiation of the actual drug delivery. Hereby, it is ensured that the procedure is not started if the drug identification retrieved is found to be abnormal.

It is noted that the processing and checking steps performed in step 411–415 are advantageous as the control of the delivery of muscle relaxant to a patient performed hereby has been found both very reliable and still performed in a simple manner which again ensures reliability. But it shall be stressed that the control may be performed in other ways as well. For example, the volume/time limit test of step 412 may be performed in step 414 as well. Further, more or less steps could be included in the control algorithm if desired.

Figure 5:
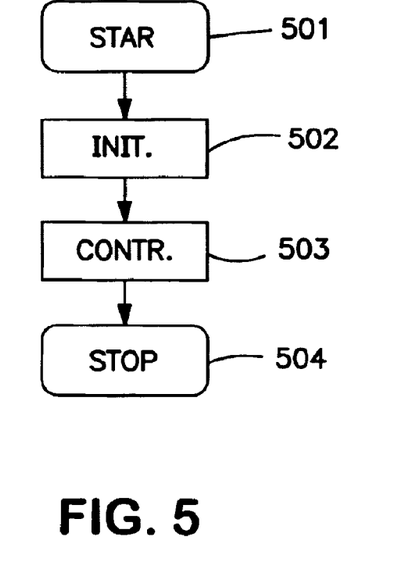
FIG. 5 illustrates a preferred control of the delivery of muscle relaxant and an initialisation thereof.

FIG. 5 is an example of the control of a system adapted for delivering muscle relaxant according to the invention, and the initialisation of such a system. In step 501, the control of system is started, e.g. when starting up the system or prior to the use of the system on a new patient. In step 502, the system is initialised. The initialisation may include inputting patient specific information into the system, e.g. via an input pad such as the keyboard 107, retrieving drug identification information, e.g. by use of identification mean 202 as described in connection with FIG. 2. Further, an array of control values may be selected from a plurality of control arrays of control values accessible by the system; i.e. the arrays may for example be located in the memory 105A and/or the memory 105B. During the initialisation in step 502, the selection of the array is performed by use of the drug identification information, the user specific information, and/or the type of intervention to be performed. The selection based may be performed automatically by the system, e.g. by a table-lookup when the selection is based on drug identification information and/or some patient information, whereas the selection may be performed manually by a user, e.g. via an input means, such as a keyboard, when the selection is based on the type of intervention to be performed or patient information indicating an abnormal and/or a critical situation. In such a situation, an alarm may be activated. For example, an alarm may be activated when the drug to be used is not usable for the actual patient. Such a test may for example be performed during initialisation of the system by performing a table look-up in a table defining non-acceptable combinations of drug and patient types and the like. Further, in a preferred embodiment the limit value used in connection with the boundary check in step 414 is set using the drug identification information and/or the user specific information. It is noted, as an alternative to the weight and concentration adaptation performed in step 413, such an adaptation or a part thereof may also be performed during the initialisation step 502.

Preferably, said measuring means is adapted for detecting a possible direct stimulation of the muscle which may occur, eg. due to a non-optimal location of stimulation means on the patient. Direct muscle stimulation, which circumvents the normal neuromuscular transmission pathway, is a situation that often shows up during use in the clinic. When direct stimulation is present this will lead to an underestimation of the muscle relaxation level, which again may lead to an overdosing of the patient. A system that can detect and warn the user about a possible direct stimulation will improve the safety when using muscle relaxation drugs. By using a number of succeeding electric or magnetic stimulation pulses, instead of the commonly used single stimulation pulse, and hereafter analysing the ratios, fade or alike of these pulses it is made possible to detect and warn about a possible direct stimulation. Such detection can be performed by comparing the measured responses with the corresponding responses that are valid or normal when no direct stimulation is present at the given relaxation level. Hereby a possible direct stimulation can be detected and signalled to the user of the system.

Figure 7:
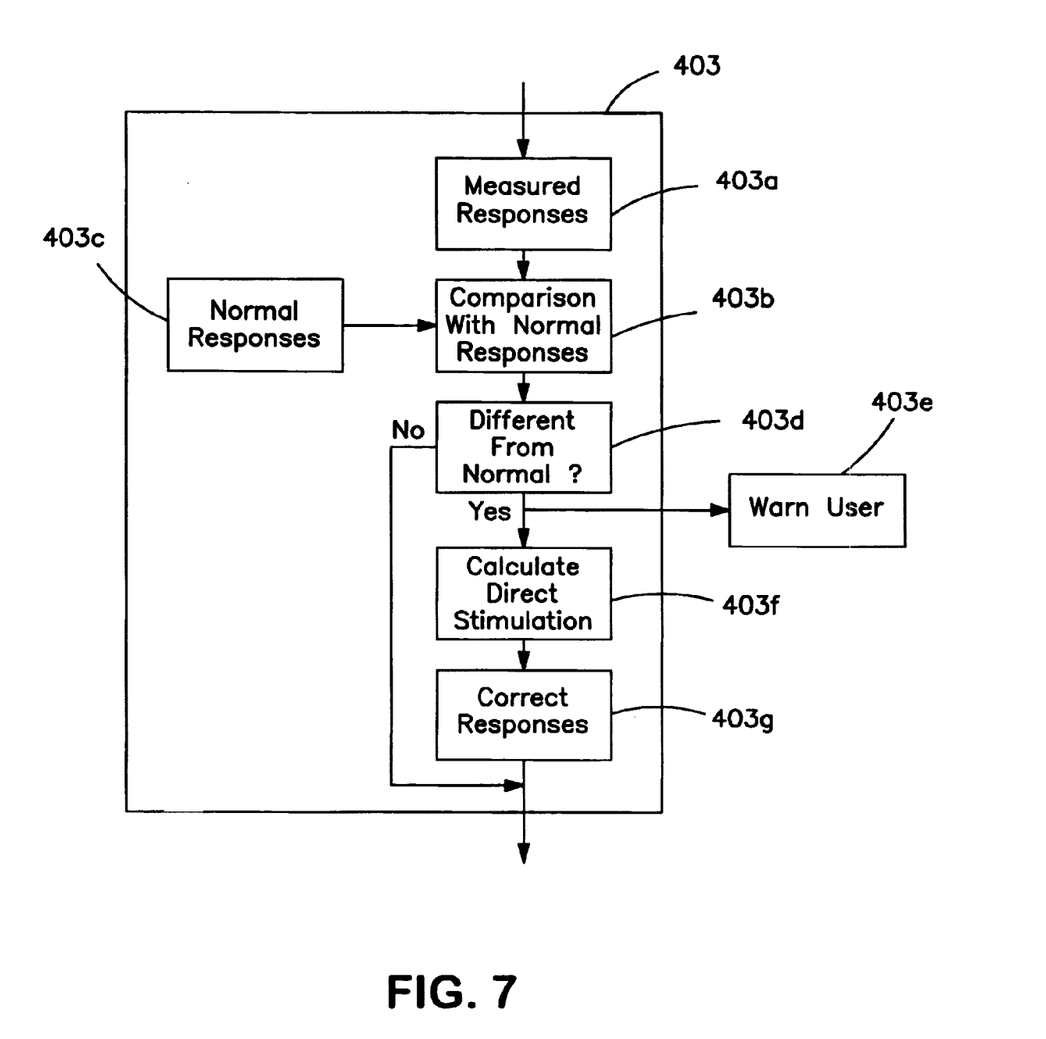
FIG. 7 is an example of a determination and correction of a measured effect of direct muscle stimulation.

Preferably, as illustrated in FIG. 7, the above-mentioned measurement of the state of relaxation (step 403 in FIG. 4) may be performed in a way in which the effect of direct muscle stimulation is taken into account. As described in the following, the effect of direct stimulation may be determined when a muscle is stimulated by a number of succeeding electric pulses. Further, as shown in FIG. 7, the detected information may be used to correct the measured relaxation of the muscle and hereby obtain a more reliable result reflecting the actual relaxation. The system according to the invention is adapted for performing the described methods.

In the example shown in FIG. 7, the method includes a first step 403a in which a muscle of the patient is stimulated by a number of succeeding electric or magnetic pulses. The resulting muscle reaction pulses are measured as described above. In step 403b two or more measured muscle reaction pulses, a representation thereof or information derived therefrom are compared with the corresponding information of reference muscle reaction pulse, i.e. information reflecting muscle reaction pulses when no direct stimulation occurs. The reference information, i.e. information reflecting one or more so-called normal responses when supplying a patient with the given stimulation, is retrieved in step 403c.

In the shown embodiment the normal responses are determined prior to use of the system and information reflecting the normal responses is stored in the memory of the system. In order to determine the normal responses without any direct stimulation present, a large number of data sets describing a pharmacokinetic, pharmacodynamic patient model, i.e. a PK/PD-model, for a number of different persons are used. The PK/PD-model, which is known from the prior art, describes a given body's influences on a given drug supplied thereto (the pharmacokinetic part of the model), and how a given body reacts to a given drug concentration (the pharmacodynamic part of the model).

As mentioned above, the measured responses and the normal responses are compared in step 403b and the difference there between is used in step 403d wherein it is determined whether the measured responses correspond with the responses of a normal situation. If this is the case no further steps have to be performed and the measured response may therefore be used as an input for said controller, i.e. the measured response may be used as a measurement of the muscle relaxation. On the other hand, if an abnormal situation occurs, i.e. the measured responses and the normal responses are found to reflect different levels of relaxation, the user of the system is given a waring (step 403e). In step 403f the effect of direct stimulation is determined. The determination may for example be calculated by comparing the measured ratios, fade or alike to a number of succeeding stimulation pulses and with the responses that are present for the same muscle relaxation level without direct stimulation. As described in connection with step 403g, the measured responses can then be corrected to a value more truly representing the correct muscle relaxation level without direct stimulation influence and the corrected value can then be used as an input for said controller.

In step 403g the responses are corrected by subtracting said effect of direct muscle stimulation from the measured effect of said muscle relaxant delivered to the patient. The system according to the invention may be adapted to perform the correction in the following way. The measured number of resulting pulses is corrected to a value more correctly representing the level of muscle relaxation without direct stimulation being present.

Figure 6:
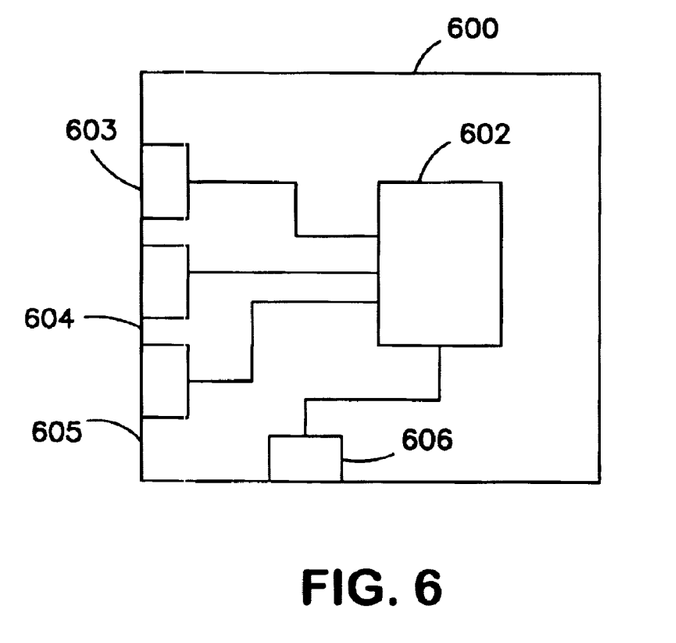
FIG. 6 is a test system according to the invention.

FIG. 6 illustrates a test system 600 for testing a system for automatic administration of muscle relaxant to a patient according to the invention. The test system 600, which is also called a patient simulator or an artificial patient (AP) in the following, emulates physical patient responses to the infusion of a muscle relaxant and the use of a neuromuscular transmission monitor.

This artificial patient includes interfaces corresponding to those of a real patient. As will be described in the following, the main units of the artificial patient are a balance or a flow measuring device measuring the infused amount of muscle relaxant over time, the variable skin resistance measuring the electrical stimulation by the system and emulating the skin (electrode) contact, an incubator emulating the skin temperature of the patient to interface with the skin temperature sensor of the system and an acceleration generator, a force generator, a sound generator or an electromyography generator emulating the muscle signal resulting from the muscle contraction or reaction of the patient. The muscle signal will be calculated from the measurements by software that consists of a pharmacokinetic, pharmacodynamic patient model developed for the purpose.

The patient simulator 600 includes a test controller 602, an input emulator 603, such as a weighing instrument or a flow measuring device, a skin temperature emulator 604, a response emulator 605, such as an acceleration generator, a force generator, a sound generator or an electromyography generator, and a variable skin resistance emulator 606. The patient simulator 600 is adapted to interact with a system for administering muscle relaxant to a patient according to the invention. Therefore, the input emulator 603 is adapted to be connected with the output of the infusion pump 102, whereas the skin temperature emulator 604, the response emulator 605, and the variable skin resistance emulator 606 are adapted to be connected with the measuring means 103.

When an electrical stimulation is applied to the skin resistance emulator 606, the artificial patient will emulate/generate a movement/reaction (muscle contraction/reaction) of the response emulator 605 which can be measured by the same kind of transducer normally applied to a real patient being monitored. If the AP receives muscle relaxants by infusion, i.e. if muscle relaxant is received by the input emulator 603, the AP will response to the stimulation and the response will depend on the stimulation given, the set skin/body temperature, the amount of drug infused and the time since infusion. Furthermore, the AP will emulate the surface temperature of the patient, as this is an important factor, which influences the muscle contraction responses. In other words, the AP behaves like a real patient.

Compared to the state of the art pre-clinical/clinical testing, a larger number of tests cases, including abnormal situations and stability, can be simulated and tested by means of the AP, in a way that is normally not possible. In addition a well-documented verification record can be obtained when using the AP in tests. This is a major improvement in validation of system safety and efficacy compared to systems according to the prior art. The control and registration mechanisms of the AP may advantageously be used for initial testing of the system pilots and 0-series before these are tested on real patients to demonstrate the safety and efficacy of the systems. Further, the AP may advantageously be used for training and educating users in how a system for administering muscle relaxant to a patient is optimally operated, e.g. prior to using the system on real patients.

The evaluations performed with the artificial patient specifically allow verification of the system stability and of hazard analysis actions, in a way that is not possible during clinical trials.

The test system according to the invention enables an evaluation and validation of the widest possible range of patient, interactions in a pre-clinical in-vitro setting.

While a preferred embodiment of the invention has been illustrated and described herein, it will be apparent to those skilled in the art that modifications and improvements may be made to forms herein specifically disclosed. Accordingly, the present invention is not to be limited to the forms therein specifically disclosed. For example, the system may be included in other instruments used in relation to surgical procedures.

What is claimed is:

1. A system for administering muscle relaxant to a patient, said system including:
   an infusion pump adapted for delivering said muscle relaxant to a patient,
   a controller adapted for controlling the operation of said infusion pump on the basis of at least one received input value, and
   measuring means adapted for continuously measuring the effect of said muscle relaxant on the patient, and adapted for supplying a value representing said measured effect as said input value to said controller, wherein on basis of said at least one input value, said controller is adapted for selecting a control value from a set of predetermined control values as the value to be used for controlling said infusion pump, characterised in that said measuring means is adapted for stimulating a muscle of the patient by a number of succeeding electric or magnetic pulses, for measuring the resulting muscle reaction pulses and for using the number of muscle reaction pulses as said input value.

2. A system according to claim 1, characterised by including a memory with an array of one or more dimensions holding said set of predefined control values, where said controller is adapted for selecting a control value from said set of control values by indexing said array by said at least one input value and/or at least one value derived therefrom.

3. A system according to claim 2, characterised in that said array is adapted for including one or more mathematical functions as a representation of a number of said control values.

4. A system according to claim 1, characterised in that said controller is adapted for selecting the control value or a representation thereof on the basis of at least one index value derived from two or more previously received input values.

5. A system according to claim 4, characterised in that said at least one index value includes a value derived as the mean value of two or more previously received input values.

6. A system according to claim 1, characterised in that said measuring means is adapted for comparing two or more of said measured muscle reaction pulses with two or more corresponding reference muscle reaction pulses or a representation thereof, and determining the difference there between as an effect of direct muscle stimulation.

7. A system according to claim 1, characterised in that said system is adapted for subtracting said effect of direct muscle stimulation from the measured effect of said muscle relaxant delivered to the patient.

8. A system according to claim 1, characterised in that said infusion pump is adapted for incepting a container including muscle relaxant and for delivering muscle relaxant from said container to a patient and by further including identification means adapted for identifying the container incepted in the infusion pump.

9. A system according to claim 8, characterised in that said controller includes a plurality of sets of control values, and said controller is adapted for selecting a set of control values to be used on the basis of the identification of the container incepted in the infusion pump.

10. A system according to claim 8, characterised in that said controller includes a plurality of sets of control values, and said controller is adapted for selecting a set of control values to be used on the basis of a received value representing the type of intervention performed or to be performed or is dependent upon certain specific patient characteristics.

11. A method of administering muscle relaxant to a patient, said method including:
    delivering said muscle relaxant to a patient, where delivery is controlled on the basis of at least one received input value, and
    continuously measuring the effect of said muscle relaxant on the patient, and supplying a value representing said measured effect as said input value for said controlling, characterised in that
    said controlling is performed using a set of predetermined control values and further including
    selecting of a control value from said set of control values as the value to be used for controlling said infusion pump, where said selection is based on said input value and/or a value derived therefrom.

12. A method according to claim 11, characterised in that said value selection is performed on the basis of at least one index value derived from two or more previously received input values.

13. A method according to claim 12, characterised in that said at least one index value is determined as the mean value of two or more previously received input values.

14. A system according to claim 9, characterised in that said controller includes a plurality of sets of control values, and said controller is adapted for selecting a set of control values to be used on the basis of a received value representing the type of intervention performed or to be performed or is dependent upon certain specific patient characteristics.

* * * * *